(12) United States Patent
Chewter et al.

(10) Patent No.: US 8,049,054 B2
(45) Date of Patent: Nov. 1, 2011

(54) PROCESS FOR THE PREPARATION OF $C_5$ AND/OR $C_6$ OLEFIN

(75) Inventors: Leslie Andrew Chewter, Amsterdam (NL); Michiel Johannes Franciscus Maria Verhaak, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 130 days.

(21) Appl. No.: 12/301,164

(22) PCT Filed: May 16, 2007

(86) PCT No.: PCT/EP2007/054753
§ 371 (c)(1),
(2), (4) Date: Dec. 8, 2008

(87) PCT Pub. No.: WO2007/135053
PCT Pub. Date: Nov. 29, 2007

(65) Prior Publication Data
US 2009/0187057 A1    Jul. 23, 2009

(30) Foreign Application Priority Data
May 19, 2006    (EP) .................................... 06114279

(51) Int. Cl.
*C07C 6/00*    (2006.01)
(52) U.S. Cl. ......... 585/643; 585/638; 585/639; 585/640
(58) Field of Classification Search .................. 585/638, 585/639, 640, 643
See application file for complete search history.

(56) References Cited

U.S. PATENT DOCUMENTS

| | | | |
|---|---|---|---|
| 679,851 A | 8/1901 | Leckband | |
| 1,351,424 A | 8/1920 | Jenkins | |
| 3,732,326 A * | 5/1973 | Chen | 585/820 |
| 4,076,796 A | 2/1978 | Reh et al. | 423/659 |
| 4,076,842 A * | 2/1978 | Plank et al. | 423/704 |
| 4,197,185 A | 4/1980 | Le Page et al. | 208/71 |
| 4,397,827 A | 8/1983 | Chu | 423/326 |
| 4,544,792 A | 10/1985 | Smith et al. | 545/533 |
| 4,556,477 A | 12/1985 | Dwyer | 208/111 |
| 4,590,320 A | 5/1986 | Sapre | 585/324 |
| 4,626,415 A | 12/1986 | Tabak | 422/190 |
| 4,665,249 A | 5/1987 | Mao et al. | 585/408 |
| 4,684,757 A | 8/1987 | Avidan et al. | 585/331 |
| 5,210,364 A * | 5/1993 | Barri et al. | 585/640 |
| 5,367,100 A | 11/1994 | Gongwei et al. | 585/640 |
| 5,534,135 A * | 7/1996 | Dai et al. | 208/120.01 |
| 5,817,906 A | 10/1998 | Marker et al. | 585/640 |
| 6,046,372 A | 4/2000 | Brown et al. | 585/640 |
| 6,307,117 B1 | 10/2001 | Tsunoda et al. | 585/651 |
| 6,339,181 B1 | 1/2002 | Chen et al. | 585/653 |
| 6,372,949 B1 * | 4/2002 | Brown et al. | 585/639 |
| 6,517,807 B2 | 2/2003 | Verduijn et al. | 423/709 |
| 6,656,345 B1 | 12/2003 | Chen et al. | 208/120.01 |
| 6,791,002 B1 | 9/2004 | Abrevaya et al. | 585/648 |
| 6,858,129 B2 | 2/2005 | Mohr et al. | 208/120.01 |
| 6,951,968 B1 | 10/2005 | Dath et al. | 585/653 |
| 6,977,321 B1 | 12/2005 | Dath et al. | 585/653 |
| 7,112,307 B2 | 9/2006 | Abrevaya et al. | 422/142 |
| 7,314,964 B2 | 1/2008 | Abrevaya et al. | 585/651 |
| 2002/0063082 A1 | 5/2002 | Touvelle et al. | 208/134 |
| 2003/0078463 A1 | 4/2003 | Martens et al. | 585/638 |
| 2003/0125598 A1 | 7/2003 | Chisholm et al. | 585/640 |
| 2003/0181777 A1 | 9/2003 | Powers et al. | 585/648 |
| 2004/0015028 A1 | 1/2004 | Brown et al. | 585/520 |
| 2005/0070422 A1 | 3/2005 | Chen et al. | 502/64 |
| 2005/0130832 A1 | 6/2005 | Abrevaya et al. | 502/4 |
| 2006/0020155 A1 | 1/2006 | Beech, Jr. et al. | 585/639 |
| 2006/0135834 A1 | 6/2006 | Xu et al. | 585/639 |
| 2009/0105429 A1 | 4/2009 | Chewter et al. | 526/67 |

FOREIGN PATENT DOCUMENTS

| | | |
|---|---|---|
| DE | 10027159 | 12/2001 |
| DE | 10043644 | 3/2002 |
| EP | 0088494 | 1/1983 |
| EP | 109059 | 5/1984 |
| EP | 0340576 | 8/1989 |
| EP | 0343454 | 11/1989 |
| EP | 0489497 | 11/1991 |
| EP | 485145 | 5/1992 |
| EP | 0596256 | 10/1993 |
| EP | 788838 | 8/1997 |
| EP | 921181 | 6/1999 |
| GB | 663901 | 12/1951 |
| WO | WO 9302994 A1 * | 2/1993 |
| WO | WO9522516 | 8/1995 |
| WO | WO9957085 | 11/1999 |
| WO | WO9957226 | 11/1999 |
| WO | WO0026163 | 5/2000 |
| WO | WO0123500 | 4/2001 |
| WO | WO0129152 | 4/2001 |

(Continued)

OTHER PUBLICATIONS

Meier, et al: "Atlas of Zeolite Structure Types Passage", Atlas of Zeolite Framework Types, 2001, pp. 9-20.
Weissermehl, K., et al., Industrial Organic Chemistry, 3$^{rd}$ Edition, Wiley, 1997, pp. 14-27.
Ch. Baerlocher, et al., Database of Zeolite Structures: http://www.iza-structure.org/databases/.

(Continued)

*Primary Examiner* — In Suk Bullock
*Assistant Examiner* — Bradley Etherton

(57) ABSTRACT

Process for the preparation of $C_5$ and/or $C_6$ olefins from a lower olefin, which lower olefin comprises from 2 to 5 carbon atoms, and an oxygenate, which oxygenate comprises at least one oxygen-bonded alkyl group, comprising contacting the lower olefin with the oxygenate, in a molar ratio of oxygen-bonded alkyl group to lower olefin of at least 1:1 in the presence of a MTT-type zeolite.

9 Claims, No Drawings

FOREIGN PATENT DOCUMENTS

| | | |
|---|---|---|
| WO | WO0134730 | 5/2001 |
| WO | WO0162689 | 8/2001 |
| WO | WO0181280 | 11/2001 |
| WO | WO0185872 | 11/2001 |
| WO | WO0190279 | 11/2001 |
| WO | WO0210098 | 2/2002 |
| WO | WO03020667 | 3/2003 |
| WO | WO2004018089 | 3/2004 |
| WO | WO2004018392 | 3/2004 |
| WO | WO2004031327 | 4/2004 |
| WO | WO2004037950 | 5/2004 |
| WO | WO2004056944 | 7/2004 |
| WO | WO2005016856 | 2/2005 |
| WO | WO2005028594 | 3/2005 |
| WO | WO2006020083 | 2/2006 |
| WO | WO2007135052 | 11/2007 |

* cited by examiner

PROCESS FOR THE PREPARATION OF $C_5$ AND/OR $C_6$ OLEFIN

PRIORITY CLAIM

The present application claims priority to European Patent Application 06114279.0 filed 19 May 2006.

TECHNICAL FIELD OF THE INVENTION

This invention relates to a process for the preparation of $C_5$ and/or $C_6$ olefins from a lower olefin and an oxygenate.

BACKGROUND OF THE INVENTION

It is known that higher olefins can be prepared by alkylating a lower olefin with an oxygenate.

For example, EP-A-0485145 describes a process for the production of olefins, selective towards $C_4/C_5$ olefins, which comprises passing an oxygenate containing feedstock over a zeo type catalyst at a temperature greater than 200° C., wherein the feedstock comprises $C_3$ and/or $C_4$ olefins and the oxygenate can be methanol, formaldehyde or dimethylether. The molar ratio of olefin to oxygenate is greater than 1:20 and the zeo type catalyst is of the TON-type structure. In the examples 1-butene and methanol are converted at temperatures of 300° C. and 400° C. over a so-called theta-1 zeolite, having a silica to alumina ratio of 68. A molar ratio of methanol to olefin of about 4:1 is exemplified. The selectivity towards $C_6+$ ranges between 43.1 and 48.4% based on carbon molar converted. This $C_6+$ product, however, also contains $C_7+$ compounds.

US-A-2003/0181777 describes a method for reducing the formation of undesired heavy hydrocarbons when catalytically cracking a heavy olefin containing feedstock to a light olefin product by employing an oxygen containing hydrocarbon as a co-feedstock. A preferred feed consists of $C_4$ and/or $C_5$ olefins. The molar ratio of oxygen containing hydrocarbon to olefinic feed is preferably less than about 1/1. In example 2, methanol and butenes are co-fed over a MTT type zeolite at a temperature of 1022-1160° F. (550-627° C.) and a methanol/olefinic stream mole ratio of about 0.77 to prepare ethylene and propylene. The examples do not show the preparation of any $C_5$ and/or $C_6$ olefins.

It would be advantageous to have a process with an increased selectivity towards $C_5$ and/or $C_6$ olefins.

SUMMARY OF THE INVENTION

Such a process has now been found by using a specific catalyst, i.e. a catalyst comprising a MTT-type zeolite. Accordingly, the present invention provides a process for the preparation of $C_5$ and/or $C_6$ olefins from a lower olefin, which lower olefin comprises from 2 to 5 carbon atoms, and an oxygenate, which oxygenate comprises at least one oxygen-bonded alkyl group, comprising contacting the lower olefin with the oxygenate, in a molar ratio of oxygen-bonded alkyl group to lower olefin of at least 1:1 in the presence of a MTT-type zeolite.

As illustrated in the examples such a process has an improved selectivity towards $C_5$ and/or $C_6$ olefins.

The process of the invention may further result in a decreased production of aromatic byproducts, such as for example benzene, even to such an extent that no benzenes may be detected in the product.

DETAILED DESCRIPTION OF THE INVENTION

The feedstock for the process includes both a feed of lower olefin and a feed of oxygenate.

By a lower olefin is understood an olefin having at least one carbon atom less than the product olefin that is to be prepared. Preferably the lower olefin has one or two carbon atom less than the desired product olefin. The desired product olefins are $C_5$ olefin and/or $C_6$ olefins. More preferably the lower olefin has just one carbon atom less then the desired product olefin.

In a preferred embodiment the process of the invention is a process to prepare $C_6$ olefins from a feed comprising at least one $C_2$-$C_5$ olefin and an oxygenate. For the preparation of a $C_6$-olefin, the lower olefin can be any $C_2$ to $C_5$ olefin. The feed of lower olefin for the preparation of a $C_6$ olefin can also comprise a mixture of $C_2$-$C_5$ olefins. Preferably the lower olefin feed for the preparation of a $C_6$ olefin comprises $C_5$-olefins and/or a mixture of $C_4$ and/or $C_5$ olefins.

In another preferred embodiment the process of the invention is a process to prepare a mixture of $C_5$ and $C_6$ olefins from a feed comprising at least one $C_2$-$C_4$ olefin and an oxygenate. For the preparation of a mixture of $C_5$ and $C_6$ olefins, such a lower olefin can be any $C_2$ to $C_4$ olefin. The feed of lower olefin for the preparation of a mixture of $C_5$ and $C_6$ olefins can also comprise a mixture of $C_2$-$C_4$ olefins. Preferably the lower olefin feed for the preparation of a mixture of $C_5$ and $C_6$ olefins comprises $C_4$ olefins.

The lower olefin may be any $C_2$-$C_5$ olefin known to the skilled person. Linear, branched and cyclic olefins may be used. Preferably, however, the lower olefin is a linear or branched, non-cyclic olefin. Furthermore all possible cis- and trans-stereo-isomers of the various $C_5$ and $C_6$ olefin isomers can be used. Preferably the lower olefin is a mono-olefin, i.e. having just one double bonding between two carbon atoms.

Examples of lower olefins include ethene; propene; 1-butene; 2-butene; 2-methyl-propene (iso-butene); 1-pentene; 2-pentene; 2-methyl-1-butene; 3-methyl-1-butene; 2-methyl-2-butene; and cyclopentene. Of these $C_4$ and/or $C_5$ olefins and any mixtures thereof are preferred.

The lower olefin may be present in admixture with saturated compounds, such as for example butanes or pentanes, or diolefins, such as 1,3-butadiene, 1,3-pentadiene or cyclopentadiene. Preferably, however, the presence of such other compounds is limited. More preferably the feed of lower olefin consists for at least 70% mol/mol, even more preferably for at least 90% mol/mol, and still more preferably for at least 95% mol/mol of mono-olefins. Most preferably the feed of lower olefin consists essentially 100% of mono-olefins.

When the lower olefin feed is a mixture of olefins, such feed preferably comprises at least 50% mol/mol, more preferably at least 80% mol/mol, even more preferably at least 90% mol/mol and most preferably between essentially 95% and 100% mol/mol of $C_4$ and/or $C_5$ olefins.

By an oxygenate comprising at least one oxygen bonded alkyl group is understood a compound comprising carbon atoms, hydrogen atoms and at least one oxygen atom, wherein at least one carbon atom is bonded to the oxygen atom via a single or a double bond, preferably via a single bond. The oxygen-bonded alkyl group preferably comprises 1 to 4 carbon atoms, more preferably 1 or 2 carbon atoms and most preferably 1 carbon atom. The oxygenate can comprise one or more of such oxygen-bonded $C_1$-$C_4$ alkyl groups. Preferably, however, the oxygenate comprises one or two oxygen-bonded $C_1$-$C_4$ alkyl groups. Examples of preferred oxygenates include alcohols, such as methanol, ethanol, isopropanol, ethylene glycol, propylene glycol; and ethers, such as dimethylether, diethylether, methylethylether, tetrahydrofuran and dioxane.

Preferably the oxygenate is chosen from the group of dimethylether, diethylether, methylethylether, methanol, ethanol and isopropanol.

More preferably an oxygenate is used having at least one oxygen-bonded $C_1$ or $C_2$ alkyl group, still more preferably at least one oxygen-bonded $C_1$ group. Most preferably the oxygenate is methanol or dimethylether.

In a preferred embodiment, where the oxygenate is methanol, such methanol is obtained from natural gas. For example by a process as described in Industrial Organic Chemistry 3rd edition page 28.

In another preferred embodiment the oxygenate is obtained through fermentation of biomaterials. For example by a process as described DE-A-10043644.

The preferred molar ratio of oxygenate to lower olefin depends on the specific oxygenate used and the number of reactive oxygen-bonded alkyl groups therein. An alcohol compound comprises one such oxygen-bonded alkyl group, whereas an ether comprises two such oxygen-bonded alkyl groups.

Preferably the ratio of mol oxygen-bonded alkyl groups to mol lower olefin lies in the range of 10:1 to 1:1, more preferably in the range of 5:1 to 1:1 and still more preferably in the range of 3:1 to 1:1. In a preferred further embodiment a molar ratio is used of more than 1:1, more preferably a ratio of 1.5:1.

In a preferred embodiment wherein the oxygenate comprises only one oxygen-bonded alkyl group, such as for example methanol, the molar ratio of oxygenate to lower olefin preferably lies in the range from 10:1 to 1:1 and more preferably in the range of 5:1 to 1:1. Most preferably such molar ratio lies in the range from 3:1 to 1:1. In a preferred further embodiment a molar ratio is used of more than 1:1, more preferably a ratio of 1.5:1

In another preferred embodiment wherein the oxygenate comprises two oxygen-bonded alkyl groups, such as for example dimethylether, the molar ratio of oxygenate to lower olefin preferably lies in the range of 10:2 to 1:2 and more preferably in the range of 5:2 to 1:2. Most preferably such molar ratio lies in the range from 3:2 to 1:2. In a preferred further embodiment a molar ratio is used of more than 1:2, more preferably a ratio of 1.5:2

Without wishing to be bound by any kind of theory it is thought that, based on the stoichiometry of the reaction, the preferred ratio of mol oxygen-bonded alkyl group to mol lower olefin, may depend on the difference in carbon atoms from the lower olefin used and the desired product olefin. For example, if a $C_2$ or $C_3$ olefin or a mixture thereof is used to prepare $C_5$ and/or $C_6$ olefin, a higher ratio of mol oxygen-bonded alkyl group to mol lower olefin can be desired than if a $C_5$ olefin is used to prepare a $C_6$ olefin or a $C_4$ olefin is used to prepare a $C_5$ olefin.

When a lower olefin is used having just one carbon atom less then the desired product olefin it is preferred to use a ratio of mol oxygen-bonded alkyl groups to mol lower olefin in the range from 2:1 to 1:1, and more preferred to use a ratio of about 1:1. For example when a $C_4$ lower olefin and methanol are used to prepare a $C_5$ product olefin; or a $C_5$ lower olefin and methanol are used to prepare a $C_6$ product olefin, the ratio is most preferably about 1:1.

When a lower olefin is used having more then one carbon atom less then the desired product olefin, a respective increase in the ratio of mol oxygen-bonded alkyl groups to mol lower olefin is most preferred. For example if a $C_3$ olefin and methanol are used to prepare a $C_6$ product olefin, it is preferred to use a ratio of mol oxygen-bonded alkyl groups to mol lower olefin in the range from 4:1 to 2:1, and more preferred to use a ratio of about 3:1.

The optimal temperature at which the process is carried out may depend on the specific MTT type zeolite used and the silica to alumina ratio (SAR) thereof.

When a MTT type zeolite having a SAR in the range from 10 to 80 is used, the process is preferably carried out at a temperature in the range of 225° C. to 425° C.

In a preferred embodiment, when a MTT type zeolite having a SAR in the range from 10 to 50 is used, the process is preferably carried out at a temperature in the range of 225° C. to 375° C., more preferably at a temperature in the range from 250° C. to 350° C.

In another preferred embodiment, when a MTT type zeolite having a SAR in the range from 50 to 80 is used the process is preferably carried out at a temperature in the range of 250° C. to 425° C., more preferably at a temperature in the range from 275° C. to 400° C.

When a MTT type zeolite having a SAR in the range of more than 80 to 500, and preferably more than 80 to 200 is used, the process is preferably carried out at a temperature in the range from 225° C. to 500° C.

In a further preferred embodiment, when a MTT type zeolite having a SAR in the range from more than 80 to 200 is used the process is preferably carried out at a temperature in the range of 300° C. to 450° C., more preferably at a temperature in the range from 325° C. to 425° C.

The process can be carried out at a wide range of pressures. Preferably the process is carried out at an pressure in the range from 1 to 5 bar, more preferably in the range from 1 to 3 bar.

The lower olefin feed and/or oxygenate feed may be diluted with a diluent gas. Any diluent gas known by the skilled person to be suitable for such purpose can be used. Examples of a diluent gas include argon, nitrogen and steam. For example, the hydrocarbon feed can be diluted with steam, for example in the range from 0.01 to 10 kg steam per kg hydrocarbon feed.

MTT-type zeolites are more particularly described in e.g. U.S. Pat. No. 4,076,842. For purposes of the present invention, MTT is considered to include its isotypes, e.g., ZSM-23, EU-13, ISI-4 and KZ-1.

The MTT-type zeolite preferably has a silica to alumina ratio (SAR) in the range from 10 to 500, more preferably in the range from 10 to 200, and still more preferably in the range from 20 to 150.

Preferably a zeolite in the hydrogen form is used, e.g. HZSM-23. Preferably at least 50% w/w, more preferably at least 90% w/w, still more preferably at least 95% w/w and most preferably 100% of the total amount of zeolite used is zeolite in the hydrogen form. When the zeolites are prepared in the presence of organic cations the zeolite may be activated by heating in an inert or oxidative atmosphere to remove the organic cations, for example, by heating at a temperature over 500° C. for 1 hour or more. The hydrogen form can then be obtained by an ion exchange procedure with ammonium salts followed by another heat treatment, for example in an inert or oxidative atmosphere at a temperature over 500° C. for 1 hour or more. The zeolites obtained after ion exchange with ammonium salts are also referred to as being in the ammonium form.

The zeolite can be used as such or in combination with a so-called binder material. The zeolite as such or the zeolite in combination with a binder material, are hereafter both also referred to as zeolite catalyst or catalyst.

It is desirable to provide a zeolite catalyst having good mechanical strength, because in an industrial environment the catalyst is often subjected to rough handling which tends to break down the catalyst into powder-like material. The later causes problems in the processing. Preferably the zeolite is therefore incorporated in a binder material. Examples of suitable binder materials include active and inactive materials and synthetic or naturally occurring zeolites as well as inorganic materials such as clays, silica, alumina, aluminosilicate. For present purposes, inactive materials of a low acidity, such as silica, are preferred because they may prevent unwanted side reactions which may take place in case a more acidic material, such as alumina is used. Preferably the catalyst used in the process of the present invention comprises, in addition to the zeolite, 2 to 90 wt %, preferably 10 to 85 wt % of a binder material.

The process of the present invention can be carried out in a batch, continuous, semi-batch or semi-continuous manner using conventional reactor systems such as fixed bed, moving bed, fluidized bed and the like. As a reactor any reactor known to the skilled person to be suitable for catalytic cracking can be used. Conventional catalyst regeneration techniques can be employed. The catalyst used in the process of the present invention can have any shape known to the skilled person to be suitable for this purpose, for example the catalyst can be present in the form of catalyst tablets, rings, extrudates, etc. extruded catalysts can be applied in various shapes, such as, cylinders and trilobes. If desired, spent catalyst can be regenerated and recycled to the process of the invention.

The invention will hereinbelow be further illustrated by the following non-limiting examples.

Example 1 and Comparative Example A

In this example 2-methyl-2-butene (2M2B) and dimethylether (DME) were reacted in a molar feed ratio 2M2B:DME of 2:1 over a MFI-type (comparative) and a MTT-type zeolite (according to the invention) at a temperature of 325° C. MTT-type zeolites of various silica-to-alumina ratios were used. The silica-to-alumina ratio for the MTT-type zeolites were respectively 47, 79 and 107. The silica-to-alumina ratio was 280 for the MFI type zeolite. A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 2.2 vol. % 2-methyl-2-butene, 1.1 vol. % dimethylether and 1 vol. % of water (in argon) was passed over the catalyst at atmospheric pressure (1 bar) at a flow rate of 50 ml/minute. Periodically, the effluent from the reactor was analyzed by gas chromatography (GC) to determine the hydrocarbon product composition. The hydrocarbon product composition has been calculated on a weight basis. Table 1 lists the reaction parameters together with the product composition, as determined by gas chromatography (GC). The selectivity has been calculated by the dividing the weight of hydrocarbon product i by the sum of the weight of all hydrocarbon (non-$C_5$) products.

TABLE 1

Conversion of 2-methyl-2-butene and dimethylether according to the invention (ratio of mol oxygen-bonded alkyl group to olefin in the feed of 1:1)

| Catalyst (SAR) | MFI* (280) | MTT (47) | MTT (79) | MTT (107) |
|---|---|---|---|---|
| Time on stream, hours | ~100 | ~100 | ~100 | ~100 |
| Temperature ° C. | 325° C. | 325° C. | 325° C. | 325° C. |

TABLE 1-continued

Conversion of 2-methyl-2-butene and dimethylether according to the invention (ratio of mol oxygen-bonded alkyl group to olefin in the feed of 1:1)

| Catalyst (SAR) | MFI* (280) | MTT (47) | MTT (79) | MTT (107) |
|---|---|---|---|---|
| 2M2B conversion, % | 77 | 62 | 52 | 44 |
| DME conversion, % | 68 | 96 | 72 | 52 |
| Ethylene, wt. %/ selectivity, % | 2/3 | 0.2/<1 | 0.1/~0 | 0.1/~0 |
| Propylene, wt. %/ selectivity, % | 16/25 | 12/22 | 3/7 | 3/7 |
| Butene isomers, wt. %/ selectivity, % | 25/41 | 13/23 | 4/9 | 4/10 |
| Hexene isomers, wt. %/ selectivity, % | 10/16 | 28/47 | 35/64 | 26/68 |
| Heptene isomers, wt. %/ selectivity, % | 9/16 | 5/7 | 9/14 | 6/15 |

*= comparative example

The above shows that an MTT-type zeolite generates a higher C6 olefin yield than an MFI-type zeolite.

Example 2

In this example 2-methyl-2-butene (2M2B) and dimethylether (DME) were reacted in a molar feed ratio 2M2B:DME of 2:1 over a MTT-type zeolite at a temperature of 450° C. MTT-type zeolites of various silica-to-alumina ratios were used. The silica-to-alumina ratio for the MTT-type zeolites were respectively 47, 79 and 107. The silica-to-alumina ratio was 280 for the MFI type zeolite. A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 2.2 vol. % 2-methyl-2-butene, 1.1 vol. % dimethylether and 1 vol. % of water (in argon) was passed over the catalyst at atmospheric pressure (1 bar) at a flow rate of 50 ml/minute. Periodically, the effluent from the reactor was analyzed by gas chromatography (GC) to determine the hydrocarbon product composition. The hydrocarbon product composition has been calculated on a weight basis.

Table 2 lists the reaction parameters together with the product composition, as determined by gas chromatography. The selectivity has been calculated by the dividing the weight of hydrocarbon product i by the sum of the weight of all hydrocarbon (non-$C_5$) products.

TABLE 2

Conversion of 2-methyl-2-butene and dimethylether at a higher temperature (ratio of mol oxygen-bonded alkyl group to olefin in the feed of 1:1)

| Catalyst (SAR) | MTT (47) | MTT (79) | MTT (107) |
|---|---|---|---|
| Time on stream, hours | ~120 | ~120 | ~120 |
| Temperature ° C. | 450° C. | 450° C. | 450° C. |
| 2M2B conversion, % | 67 | 62 | 60 |
| DME conversion, % | ~100 | ~100 | ~100 |
| Ethylene, wt. %/ selectivity, % | 4.5/7 | 2/3 | 1/2 |
| Propylene, wt. %/ selectivity, % | 42/66 | 31/54 | 18/32 |

TABLE 2-continued

Conversion of 2-methyl-2-butene and dimethylether at a higher temperature (ratio of mol oxygen-bonded alkyl group to olefin in the feed of 1:1)

| Catalyst (SAR) | MTT (47) | MTT (79) | MTT (107) |
|---|---|---|---|
| Butene isomers, wt. %/ selectivity, % | 14/21 | 12/21 | 10/19 |
| Hexene isomers, wt. %/ selectivity, % | 3/5 | 13/23 | 27/47 |
| Heptene isomers, wt. %/ selectivity, % | 1/2 | 1/2 | 3/5 |

Examples 3, 4 and 5

In this example 1-butene and dimethylether (DME) were reacted in molar feed ratios 1-butene:DME of 2:1, 1:1 and 2:3 over a MFI-type zeolite (comparative) and a MTT-type zeolite (according to the invention). MTT-type zeolites of various silica-to-alumina ratios were used. The silica-to-alumina ratio for the MTT-type zeolites were respectively 47, 79 and 107. The silica-to-alumina ratio was 280 for the MFI type zeolite. A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 2.0 vol. % 1-butene, respectively 0.9, 1.9 and 2.8 vol. % dimethyl-ether and 1 vol. % of water (in argon) was passed over the catalyst at atmospheric pressure (1 bar) at a flow rate of 50 ml/minute. Periodically, the effluent from the reactor was analyzed by gas chromatography to determine the hydrocarbon product composition. The hydrocarbon product composition has been calculated on a weight basis.

Tables 3, 4 and 5 list the reaction parameters together with the product composition, as determined by gas chromatography. The selectivity has been calculated by the dividing the weight of hydrocarbon product i by the sum of the weight of all hydrocarbon (non-$C_4$) products.

TABLE 3

Conversion of 1-butene and dimethylether (DME) (0.9 vol % DME; ratio of 1-butene:DME = 2:1; ratio of mol oxygen-bonded alkyl group to olefin = 1:1)

| Catalyst (SAR) | MFI (280)* | | | MTT (47) | | | MTT (79) | | | MTT (107) | | |
|---|---|---|---|---|---|---|---|---|---|---|---|---|
| Time on stream, hours | ~50 | | | ~50 | | | ~50 | | | ~50 | | |
| Temperature ° C. | 300 | 350 | 400 | 300 | 350 | 400 | 300 | 350 | 400 | 300 | 350 | 400 |
| 1-butene conversion, % | 64 | 60 | 57 | 56 | 57 | 55 | 36 | 54 | 57 | 21 | 35 | 45 |
| DME conversion | 59 | 64 | 78 | 72 | 88 | 94 | 31 | 81 | 97 | 7 | — | 56 |
| Ethylene, wt. %/ Selectivity, % | 2/4 | 1/3 | 2/5 | 0.1~0 | 1/1 | 1/4 | 0.1~0 | 0~0 | 0.2 < 1 | 0~0 | 0.1~0 | 0.1~0 |
| Propylene, wt. %/ Selectivity, % | 14/24 | 23/42 | 30/55 | 3/6 | 13/23 | 19/33 | 1/1 | 1/3 | 4/8 | 0.12 | 0.12 | 0.33 |
| Pentene isomers, wt. %/ Selectivity, % | 21/35 | 17/31 | 15/27 | 34/66 | 34/61 | 33/57 | 17/78 | 38/71 | 41/71 | 17/83 | 27/80 | 34/75 |
| Hexene isomers, wt %/ Selectivity, % | 10/17 | 7/13 | 5/9 | 11/22 | 6/11 | 1/4 | 5/14 | 12/22 | 11/19 | 2/11 | 5/16 | 9/20 |
| Heptene isomers, wt %/ Selectivity, % | 12/20 | 6/11 | 3/5 | 4/7 | 2/3 | 1/2 | 2/7 | 2/3 | 1/2 | 1/3 | 1/2 | 1/2 |
| Selectivity to $C_5$ and/or $C_6$ olefins | 52 | 44 | 36 | 88 | 72 | 61 | 92 | 93 | 90 | 94 | 96 | 95 |

*= Comparative example

TABLE 4

Conversion of 1-butene and dimethylether (DME) (1.9 vol % DME; ratio of 1-butene:DME = 1:1; ratio of mol oxygen-bonded alkyl group to olefin = 2:1)

| Catalyst (SAR) | MFI (280)* | | | MTT (47) | | | MTT (79) | | | MTT (107) | | |
|---|---|---|---|---|---|---|---|---|---|---|---|---|
| Time on stream, hours | ~20 | | | ~20 | | | ~20 | | | ~20 | | |
| Temperature ° C. | 300 | 350 | 400 | 300 | 350 | 400 | 300 | 350 | 400 | 300 | 350 | 400 |
| 1-butene conversion, % | 81 | 56 | 52 | 80 | 64 | 64 | 81 | 73 | 71 | 48 | 72 | 73 |
| DME conversion | 84 | 77 | 86 | 57 | 98 | 100 | 20 | 95 | 100 | 25 | 74 | 87 |
| Ethylene, wt. %/ Selectivity, % | 3/8 | 2/3 | 3/5 | 0.1~0 | 1/1 | 3/4 | 0.1~0 | 0.2~0 | 1/1 | 0.1~0 | 0.2~0 | 0.4 < 1 |
| Propylene, wt. %/ Selectivity, % | 5/25 | 25/38 | 36/56 | 4/5 | 22/32 | 35/47 | 1/2 | 9/12 | 18/22 | 1/3 | 5/7 | 11/11 |
| Pentene isomers, wt. %/ Selectivity, % | 10/30 | 19/29 | 13/25 | 37/48 | 35/47 | 35/41 | 21/57 | 39/47 | 40/48 | 32/69 | 42/52 | 42/48 |
| Hexene isomers, wt %/ Selectivity, % | 7/20 | 7/15 | 5/8 | 20/33 | 16/16 | 6/5 | 10/28 | 28/33 | 20/26 | 10/20 | 29/33 | 27/32 |
| Heptene isomers, wt %/ Selectivity, % | 6/17 | 7/12 | 4/6 | 8/13 | 2/4 | 2/2 | 4/10 | 7/7 | 3/3 | 4/8 | 8/8 | 5/6 |
| Selectivity to $C_5$ and/or $C_6$ olefins | 50 | 44 | 33 | 81 | 63 | 46 | 85 | 80 | 74 | 89 | 85 | 80 |

*= Comparative examples

TABLE 5

Conversion of 1-butene and dimethylether (DME) (2.8 vol % DME; ratio of 1-butene:DME = 2:3; ratio of mol oxygen-bonded alkyl group to olefin = 3:1)

| Catalyst (SAR) | MFI (280)* | | | MTT (47) | | | MTT (79) | | | MTT (107) | | |
|---|---|---|---|---|---|---|---|---|---|---|---|---|
| Time on stream, hours | ~70 | | | ~70 | | | ~70 | | | ~70 | | |
| Temperature ° C. | 300 | 350 | 400 | 300 | 350 | 400 | 300 | 350 | 400 | 300 | 350 | 400 |
| 1-butene conversion, % | 61 | 53 | 47 | 60 | 68 | 65 | 38 | 73 | 82 | 25 | 48 | 64 |
| DME conversion | 80 | 80 | 89 | 20 | 92 | 99 | 5 | 35 | 62 | 5 | 7 | 21 |
| Ethylene, wt. %/ Selectivity, % | — | 3/4 | 4/5 | 0/0 | 1/1 | 2/2 | 0~0 | 0~0 | 0.3~0 | 0/~0 | 0/~0 | 0.1~0 |
| Propylene, wt. %/ Selectivity, % | 17/21 | 27/37 | 42/55 | 1/2 | 21/21 | 38/44 | 0.3/1 | 3/3 | 7/8 | 0.2/1 | 1/2 | 2/3 |
| Pentene isomers, wt. %/ Selectivity, % | 25/33 | 22/31 | 18/23 | 41/67 | 40/40 | 36/39 | 30/77 | 45/58 | 39/43 | 21/81 | 35/72 | 40/63 |
| Hexene isomers, wt. % Selectivity, % | 15/19 | 11/16 | 8/10 | 15/23 | 31/33 | 13/12 | 6/15 | 23/30 | 33/36 | 4/15 | 10/21 | 17/27 |
| Heptene isomers, wt. %/ Selectivity, % | 13/17 | 9/12 | 5/7 | 5/7 | 7/6 | 2/3 | 3/7 | 7/9 | 11/12 | 1/3 | 3/6 | 5/8 |
| Selectivity to $C_5$ and/or $C_6$ olefins | 52 | 47 | 33 | 90 | 73 | 51 | 92 | 88 | 79 | 96 | 93 | 90 |

*= Comparative examples

Example 6 and Comparative Example B

In this example 1-butene and dimethylether (DME) were reacted in molar feed ratios 1-butene:DME of 1:2 over a TON-type zeolite (comparative) and a MTT-type zeolite (according to the invention). The silica-to-alumina ratio for the MTT-type and TON-type zeolites were 107 and 102, respectively. A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 2 vol. % 1-butene and 4 vol. % dimethyl-ether and 2 vol. % of water (in argon) was passed over the catalyst at atmospheric pressure (1 bar) at a flow rate of 50 ml/minute. Periodically, the effluent from the reactor was analyzed by gas chromatography to determine the hydrocarbon product composition. The hydrocarbon product composition has been calculated on a weight basis.

Tables 2 lists the reaction parameters together with the product composition, as determined by gas chromatography. The selectivity has been calculated by the dividing the weight of hydrocarbon product i by the sum of the weight of all hydrocarbon (non-$C_4$) products.

TABLE 6

Conversion of 1-butene and dimethylether (DME) (4 vol % DME; ratio of 1-butene:DME = 1:2; ratio of mol oxygen-bonded alkyl group to olefin = 4:1)

| Catalyst (SAR) | MTT (107) | | TON (102)* | |
|---|---|---|---|---|
| Time on stream, hours | ~5 | | ~5 | |
| Temperature ° C. | 325 | 450 | 325 | 450 |
| 1-butene conversion, % | 21 | 83 | 19 | 64 |
| DME conversion | 4.6 | 46 | 4.7 | 99 |
| Ethylene, wt. %/ Selectivity, % | 0/0.3 | 0.7/0.4 | 0/0.3 | 6.9/9.7 |
| Propylene, wt. %/ Selectivity, % | 0.1/0.8 | 3.7/6.3 | 0.1/1.1 | 44/61.6 |
| Pentene isomers, wt. %/ Selectivity, % | 8/87 | 24/41 | 7.5/89 | 14/19 |
| Hexene isomers, wt. % Selectivity, % | 0.9/10 | 22/37 | 0.7/7.9 | 3.7/5.2 |
| Heptene isomers, wt. %/ Selectivity, % | 0.1/1 | 7.3/12 | 0.1/1 | 1.6/2.2 |
| Selectivity to $C_5$ and/or $C_6$ olefins | 97 | 78 | 98 | 24 |
| Total C5 + C6 olefin yield (wt %) | 8.9 | 46 | 8.2 | 17.7 |

*= comparative

The above shows that an MTT-type zeolite generates a higher total C5+C6 olefin yield than an TON-type zeolite.

What is claimed is:

1. A process for the preparation of $C_5$ and/or $C_6$ olefins from a lower olefin, which lower olefin comprises from 2 to 5 carbon atoms, and an oxygenate, which oxygenate comprises at least one oxygen-bonded alkyl group, comprising contacting the lower olefin with the oxygenate, in a molar ratio of oxygen-bonded alkyl group to lower olefin of at least 1:1 in the presence of a MTT zeolite, wherein a MTT zeolite having a SAR in the range from 10 to 80 is used, and the process is carried out at a temperature in the range of 225° C. to 425° C.

2. The process according to claim 1, wherein the lower olefin is a $C_2$-$C_5$ olefin and a $C_6$ olefin is prepared.

3. The process according to claim 1, wherein the lower olefin is a $C_2$-$C_4$ olefin and a mixture of $C_5$ and $C_6$ olefins is prepared.

4. The process according to claim 1, wherein the molar ratio of oxygen-bonded alkyl group to lower olefin lies in the range from 10:1 to 1:1.

5. The process according to claim 1, wherein the oxygenate is an ether or an alcohol.

6. The process according to claim 5, wherein the oxygenate is methanol or dimethylether.

7. The process according to claim 1, wherein a MTT zeolite having a SAR in the range from 10 to 50 is used and the process is carried out at a temperature in the range of 225° C. to 375° C.

8. The process according to claim 1, wherein a MTT zeolite having a SAR in the range from 50 to 80 is used and the process is carried out at a temperature in the range of 250° C. to 425° C.

9. The process according to claim 1, wherein at least part of any unconverted feed is recycled.

\* \* \* \* \*